United States Patent [19]
Masuda et al.

[11] Patent Number: 4,929,076
[45] Date of Patent: May 29, 1990

[54] OPHTHALMIC MEASURING APPARATUS

[75] Inventors: Takashi Masuda, Kawasaki; Kyoji Sekiguchi, Yokohama, both of Japan

[73] Assignee: Canon Kabushiki Kaisha, Tokyo, Japan

[21] Appl. No.: 342,708

[22] Filed: Apr. 24, 1989

Related U.S. Application Data

[63] Continuation of Ser. No. 96,260, Sep. 8, 1987, abandoned, which is a continuation of Ser. No. 808,883, Dec. 13, 1985, abandoned, which is a continuation-in-part of Ser. No. 580,813, Feb. 16, 1984, abandoned.

[30] Foreign Application Priority Data

Jun. 13, 1983 [JP] Japan .................... 58-105593
Feb. 9, 1985 [JP] Japan .................... 60-23727

[51] Int. Cl.⁵ .............................. A61B 3/10
[52] U.S. Cl. .................... 351/212; 351/205; 351/211

[58] Field of Search ............... 351/205, 206, 211, 212, 351/247

[56] References Cited

U.S. PATENT DOCUMENTS 4,312,574  1/1982  Wilms .................... 351/212
4,431,218  2/1984  Nohda .................... 351/211

FOREIGN PATENT DOCUMENTS 58-29446  7/1959  Japan .

Primary Examiner—Paul M. Dzierzynski
Attorney, Agent, or Firm—Fitzpatrick, Cella, Harper & Scinto

[57] ABSTRACT

An ophthalmic measuring apparatus having a cornea shape measuring device and an eye refractive power device which are operated so that both the measurements of the shape of cornea and the eye refractive power may be effected simultaneously.

2 Claims, 4 Drawing Sheets

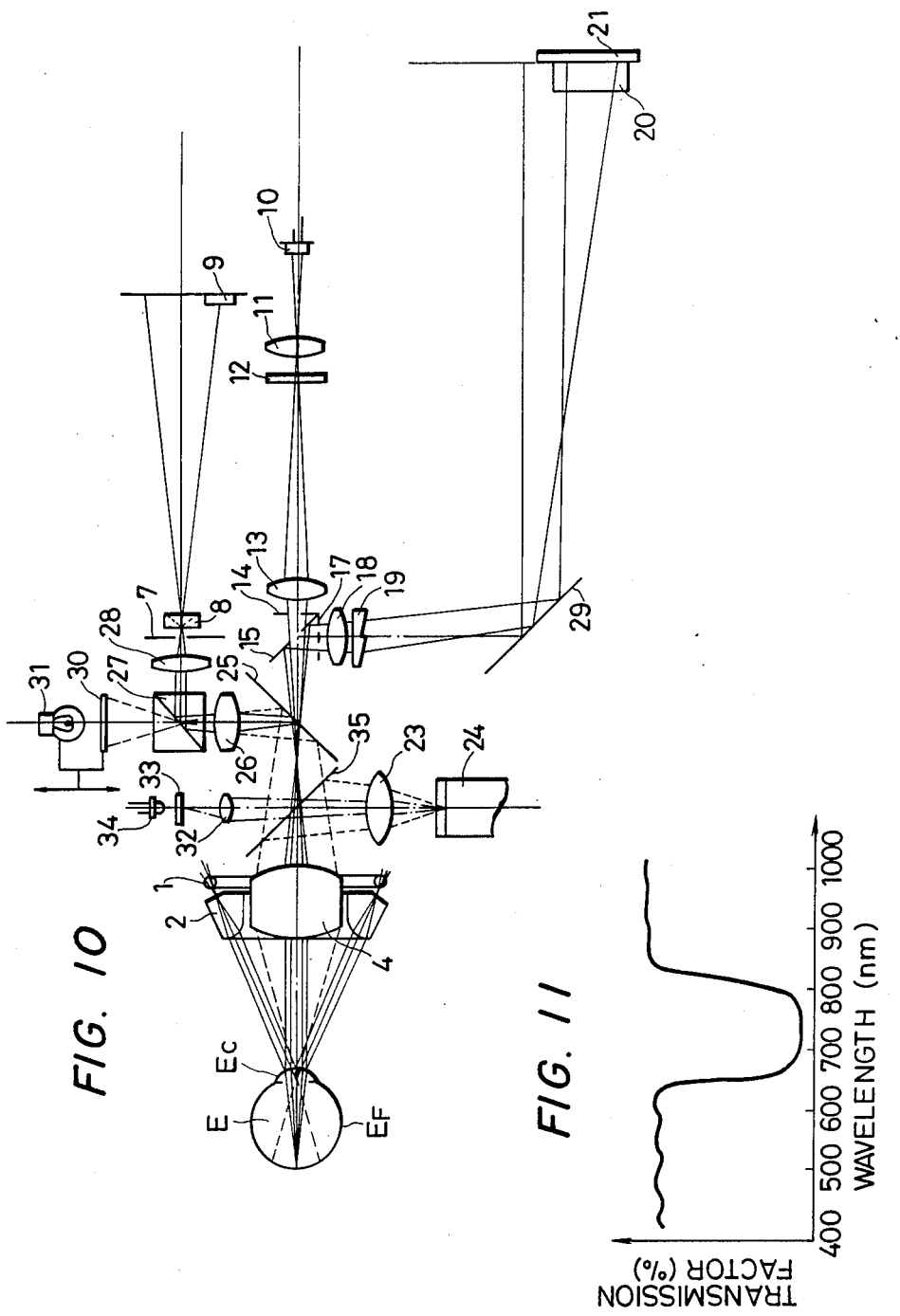

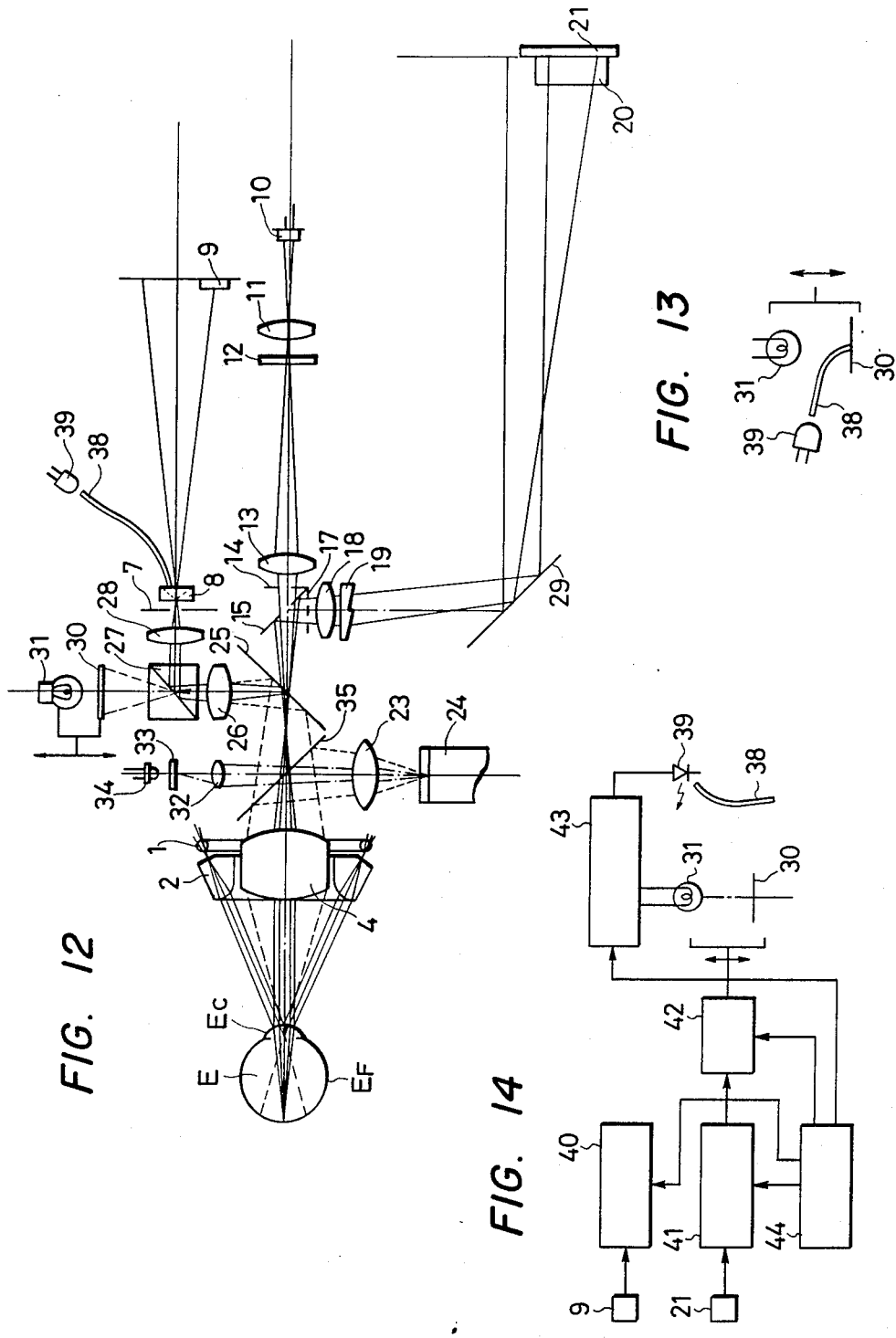

OPHTHALMIC MEASURING APPARATUS

This application is a continuation of application Ser. No. 07/096,260 filed Sep. 8, 1987, which is a continuation of application Ser. No. 06/808,883 filed Dec. 13, 1985 which is a continuation-in-part of Ser. No. 06/580,813 filed Feb. 16, 1984 all now abandoned.

BACKGROUND OF THE INVENTION

1. Field of the Invention

This invention relates to an ophthalmic measuring apparatus capable of measuring the refractive power of an eye and the shape of cornea at a time.

2. Description of the Prior Art

Generally, when examination of eye refraction is to be carried out, measurement of the shape of the cornea is also carried out for the purpose of the examination of the presence of astigmatism and of the examination of the axis of astigmatism and the degree of astigmatism. Particularly, with the recent spread of contact lenses, examination of the shape of cornea has become more important to choose the base curve thereof.

Heretofore, when such an examination is to be carried out, it has been usual to accomplish "contact lens prescription" by first measuring the shape of the cornea of the examinee by an instrument called an ophthalmometer or a keratometer, choosing the base curve and determining the degree of corneal astigmatism, thereafter screening the full refractive power and the full astigmatism by an unconscious (objective) refraction examination using a refractometer or the like, and effecting a self-conscious (subjective) refraction examination and final determination of the base curve by the trial lens method. Measurement of the shape of cornea has been proposed by U.S. patent application Ser. No. 416,355, and Japanese Laid-open Patent Application No. 161031/1981, etc. are known for the measurement of eye refractive power.

As described above, heretofore, measurement of the shape of cornea and measurement of refractive power have been carried out discretely by the use of different instruments and thus, the time and labor required for the measurements have been a considerable burden to both of the examiner and the examinee.

Presently, when overall eye refractive power is to be measured, the eye to be examined is caused to watch a fixation chart provided in the apparatus and the eye to be examined is fixed, and then a predetermined visual target is projected onto the fundus of the eye to be examined and the reflected image thereof is received by a detector, and they are analyzed to thereby obtain a measured value.

There are two kinds of fixation charts for measurement of eye refractive power, namely, a slide photograph of landscape or the like and a radial pattern. The latter radial pattern is such that the center thereof is watched. Now, when the shape of cornea is to be measured, the result of the measurement is affected more by the movement of the examinee than in the case of the measurement of eye refractive power. Therefore, it is necessary to provide a fixation chart for measurement of the shape of cornea, to cause the eye to be examined to watch the fixation chart more concentratedly and to thereby positively fix the eye to be examined.

Where a slide of landscape or the like is used as a common fixation chart for measurement of eye refractive power and for measurement of the shape of cornea, the examinee may be puzzled which portion of the slide to watch and therefore, a slide of landscape or the like is unsuitable as a fixation chart for measurement of the shape of cornea. So, there is considered a case where a radial pattern is used as a common fixation chart. However if the pattern is fixed at the orthoptic position, the pattern will be blurred and cannot be viewed in the case of an examinee of a medium or strong degree of short-sightedness or long-sightedness. Accordingly, it is difficult to fix the eye for examination.

SUMMARY OF THE INVENTION

It is an object of the present invention to overcome such problems and to provide an ophthalmic measuring apparatus which is capable of measuring the shape of cornea and the eye refractive power at a single time to thereby greatly reduce the time and labor required for the measurements and is also capable of correcting any error of movement of the eyeballs of the examinee to thereby enable accurate measurement.

It is another object of the present invention to provide an ophthalmic measuring apparatus which has no movable portion and which is capable of measuring the shape of cornea and the eye refractive power at a time.

It is still another object of the present invention to provide an ophthalmic measuring apparatus in which during the measurement of the eye refractive power and the measurement of the shape of cornea, the eye to be examined is fixed so as to be suited for each measurement to thereby enable highly accurate measurement.

The invention will become fully apparent from the following detailed description thereof taken in conjunction with the accompanying drawings.

BRIEF DESCRIPTION OF THE DRAWINGS

FIG. 10 shows a second embodiment of the present invention.

FIG. 11 is a graph showing the characteristic of a dichroic mirror.

FIG. 12 shows an embodiment in which discrete fixation charts are provided so as to be suited for measurement of the eye refractive power and measurement of the shape of cornea.

FIG. 13 shows another embodiment of the fixed visual target for measurement of the shape of cornea.

FIG. 14 is a block diagram of a control circuit concerned with the illumination of the fixation chart.

DESCRIPTION OF THE PREFERRED EMBODIMENTS

Figure 1:
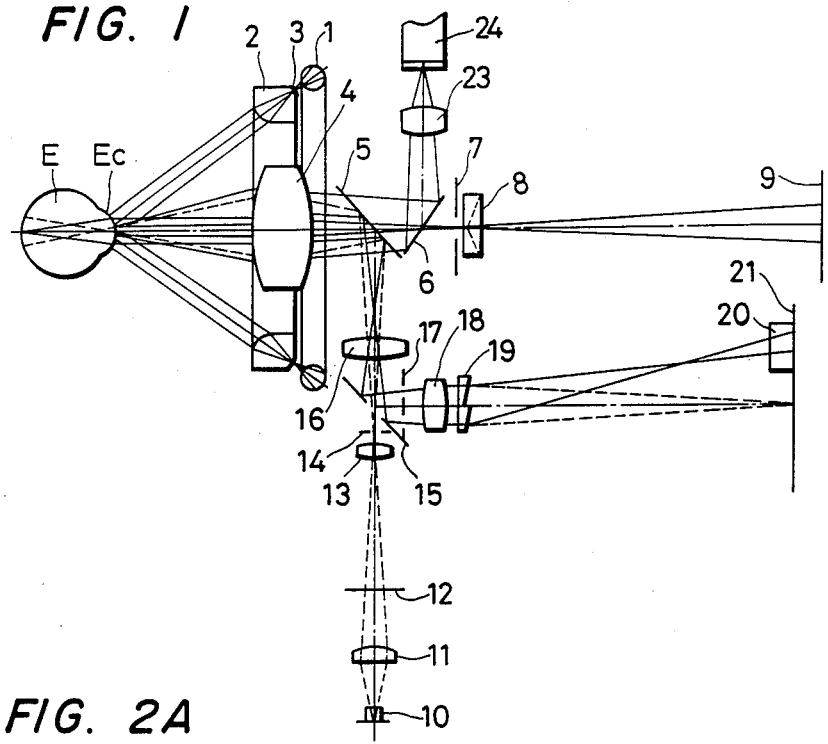
FIG. 1 shows the optical construction of a first embodiment of the present invention.

FIG. 1 shows an optical system according to an embodiment of the present invention. During measurement of the shape of the cornea, a visible light emitted from a ring-like strobo 1 may illuminated a circular slit 3 provided in a collimater ring lens 2 disposed on the side opposite to an eye E to be examined. The slit 3, when viewed in a cross-section containing the optic axis, lies on the focal plane of the ring lens 2, the slit 3 is made to lie at an optically infinite point, and a light projected from the infinite point is adapted to illuminate the cornea Ec of the eye E to be examined. Since the surface of the eye E to be examined is like a convex mirror, it makes the corneal reflection image Sa of the slit 3, and this corneal reflection image Sa passes through an objective lens 4, a dichroic mirror 5 transmitting visible light therethrough and reflecting infrared light, a half-mirror 6 and a multi-apertured stop 7 provided in the focal plane of the objective lens 4, is deflected by a prism 8 and is re-imaged on a linear position detecting element 9 called CCD.

Figure 2A:
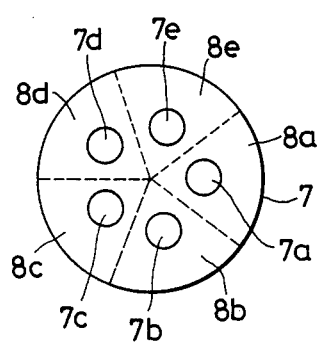
FIG. 2A is a front view of a multi-apertured stop.
Figure 2B:
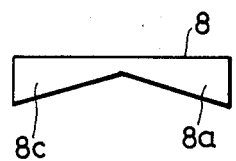
FIG. 2B is a cross-sectional view of a prism.
Figure 3:
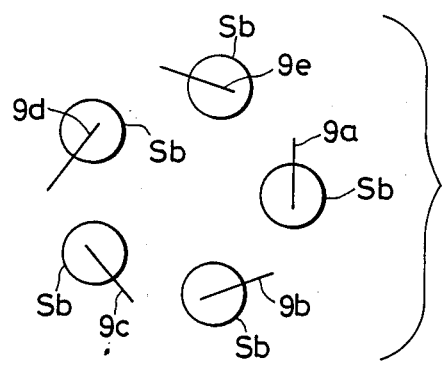
FIG. 3 illustrates the relation between the corneal reflection image and a detecting element.

The multi-apertured stop 7, as shown in FIG. 2A, has, for example, five openings 7a-7e and the prism 8 also has five elements 8a-8e divided by dotted lines of FIG. 2A correspondingly to the openings 7a-7e, each of the elements 8a-8e being of a cross-sectional shape as shown in FIG. 2B. Five corneal refelction images separated by the multiapertured stop 7 and the prism 8 are coupled together at the position of the detecting element 9 in a relation as shown in FIG. 3. In FIG. 3, Sb designates corneal reflection images into which the corneal reflection image Sa is imaged and separated by the objective lens 4, and reference characters 9a-9e denote detecting elements which respectively correspond to the openings 7a-7e and the prism elements 8a-8e. Thus, the coordinates of five points in the corneal reflection images Sb are detected, and the coordinates of these five points are substituted into the following general equation of a quadratic curve:

$$AX^2 + BXY + CY^2 + DX + EY + F = 0$$

to thereby solve simultaneous equations, whereby coefficients A–E are found and modified into the following general equation of an ellipse:

$$(x-x_0)^2/a^2 + (y-y_0)^2/b^2 = 1$$

where
$x = X \cos \theta - Y \sin \theta$
$y = X \sin \theta + Y \cos \theta$,
whereby the radii of curvature of the two main meridians of the cornea Ec are derived from the major diameter a and the minor diameter b of the ellipse and thus, the axis of astigmatism can be calculated from the angle $\theta$.

Figure 4:
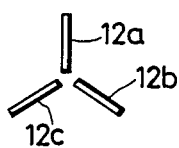
FIG. 4 is a front view of an eye fundus projection chart.

On the other hand, where the refractive power is to be measured, as shown in FIG. 1, the light from a light-emitting diode 10 which emits infrared light may pass through a condensing lens 11 and illuminate an eye fundus projection chart 12. This chart 12, as shown in FIG. 4, is provided with three slits 12a-12c extending in the directions of three meridians forming an angle of 120° with one another. The light from the light-emitting diode 10 may further pass through a relay lens 13 and may be once imaged on an eye fundus illuminating stop 14, and then may pass through an apertured mirror 15 and a relay lens 16 and may be reflected by the dichroic mirror 5 because this light is infrared light, and may be imaged on the pupil of the eye E to be examined through the objective lens 4 and illuminate the eye fundus.

Figure 5:
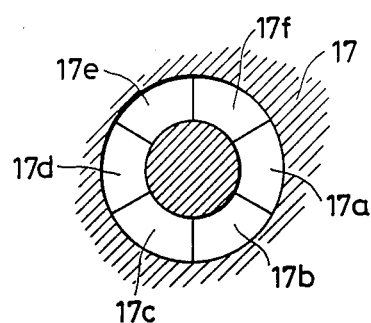
FIG. 5 is a front view of an aperture plate for measuring the eye refraction.
Figure 6:
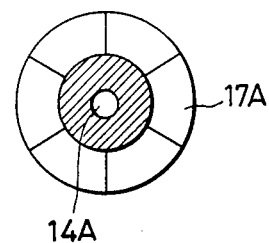
FIG. 6 is a front view showing the imaged condition of the stop on the pupil of an eye to be examined.

Also, the chart 12 is first imaged through the relay lenses 13 and 16 and projected by the objective lens 4 so as to be conjugate with the fundus of an eye in emmetropia. The reflected image from the eye fundus again passes through the objective lens 4 and is reflected and imaged by the dichroic mirror 5, and further passes through the relay lens 16 and is reflected by the apertured mirror 15. An aperture plate 17 is disposed near the apertured mirror 15 and this aperture plate 17, as shown in FIG. 5, has six openings 17a-17f each two of which correspond to each meridian direction of the chart slit 12a-12c. The openings 17a and 17d, 17b and 17e, 17c and 17f respectively form a channel. The eye fundus illuminating stop 14 and the aperture plate 17 may be imaged on the pupil of the eye E to be examined as indicated at 14A and 17A in FIG. 6 so as to separate the projecting system and the measuring system of the chart 12.

Figure 7A:
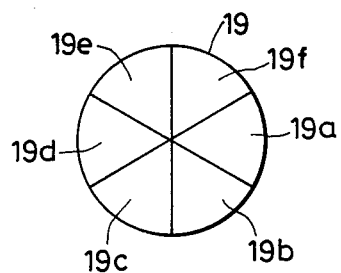
FIG. 7A is a front view of an image separating prism for measuring the eye refractive power.
Figure 7B:
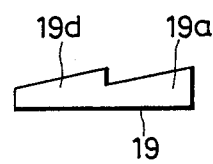
FIG. 7B is a cross-sectional view of the same prism.

The light flux divided by the aperture plate 17 may be deflected by a prism 19 through an imaging lens 18, may be condensed in the direction of the shorter length of a detecting element 21 by a cylindrical lens 20 and may be imaged on three detecting elements 21a-21c. The prism 19, as shown in FIG. 7A, has six elements 19a-19f and is adapted to separate the images correspondingly to the six openings 17a-17f of the aperture plate 17. FIG. 7B shows the cross-sectional shape of the prism 19.

Figure 8:
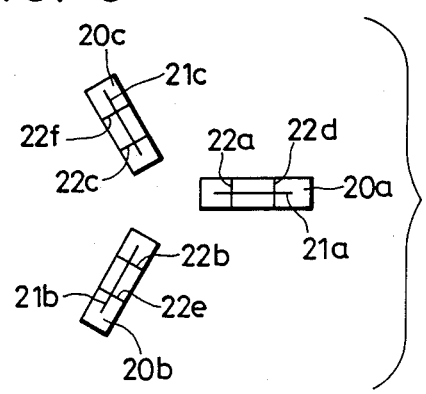
FIG. 8 illustrates the relation between the image of the eye fundus and a light-receiving element.

The images thus separated are condensed lengthwisely thereof by three cylindrical lenses 20a-20c and imaged on the detecting elements 21a-21c. FIG. 8 shows the imaged condition of the images of the eye fundus. In FIG. 8, reference characters 22a-22f designate the images of the eye fundus imaged correspondingly to the openings 17a-17f.

If the eye E to be examined is an eye out of emmetropia, the light ray having left the eye fundus and having left a certain point on the pupil emerge at an angle corresponding to the refractive power and therefore, if use is made of an optical system like the present embodiment, the interval between the two eye fundus images 22 on the detecting element 21 will vary in accordance with the refractive power of the eye E to be examined.

Accordingly, if the relation between the interval between the two eye fundus images 22 and the refractive power is found in advance, the refractive powers in three meridian directions can be measured and by substituting each of those refractive powers into the following equation $$D = A \sin^2(\omega + \theta) + B,$$

the refractive power, the degree of astigmatism and the angle of astigmatism can be calculated.

According to such an embodiment, the shape of the cornea and the refractive power can be measured without any movable portion.

The alignment between the eye E to be examined and the instrument can be accomplished by causing the front eye part to be transmitted through the dichroic mirror 5 by the objective lens 4, causing the light ray reflected by the half-mirror 6 to be imaged on a television image pickup tube 24 by a television relay lens 23 and monitoring the image by a television monitor attached to or separate from the main body.

Figure 9:
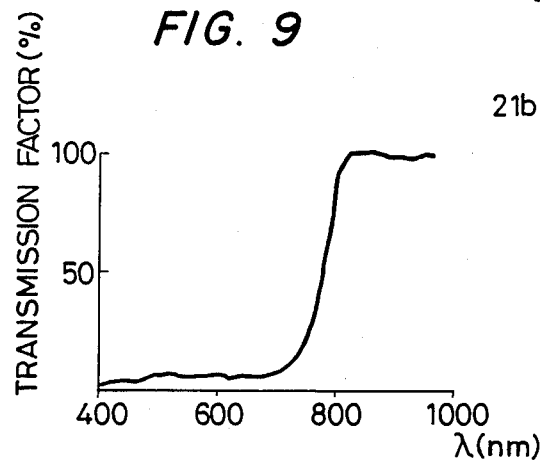
FIG. 9 is a graph showing the characteristic of a dichroic mirror.

Also, in the present embodiment, the dichroic mirror 5 used is of such a characteristic as shown in FIG. 9 which transmits visible light and reflects infrared light and the light from the light-emitting diode 10 for illuminating the eye fundus also utilizes infrared light and therefore, the dazzlement of the examinee can be reduced. However these wavelengths can be selected as desired independently of the embodiment.

FIG. 10 shows a second embodiment of the present invention. In the second embodiment, reference numerals similar to those in the first embodiment designates similar members In FIG. 10, reference numeral 25 designates a dichroic mirror reflecting visible light and transmitting infrared light therethrough, reference numeral 26 denotes a relay lens, reference numeral 27 designates a beam splitter and reference numeral 28 denotes a projection lens. The corneal reflection image is projected onto the linear position detecting element 9 through these members, the multi-apertured stop 7 and the prism 8. These together constitute a cornea shape measuring system. On the other hand, during measurement of the refractive power, the light from the light-emitting diode 10 may pass through the dichroic mirror 25 and the light reflected by the fundus of the eye to be examined may reach the detecting element 21 through the apertured mirror 15, the aperture plate 17, the imaging lens 18, the prism 19, a mirror 29 and the cylindrical lens 20.

Now, in the optical path divided by the beam splitter 27, a fixation chart 30 and a light source 31 for the fixation chart are provided so as to be movable together in the direction of the optic axis. These are used to reduce the adjustment force of the eye during measurement of the refractive power and are moved in the direction of the optic axis until the measured value of the refractive power varies no longer. That is, in a condition in which the adjustment force of the eye is acting, the measured value of the refractive power varies in conformity with the movement of the fixation chart 30 in the direction of the optic axis, but when the fixation chart reaches a position in which the adjustment force of the eye does not act, the measured value of the refractive power varies no longer even if the fixation chart is further moved from that position in the direction of the optic axis.

The direction and amount of movement of the fixation chart 30 are suitably determined on the basis of the then measured value of the refractive power.

In FIG. 10, reference numeral 35 designates a dichroic mirror having such a spectral transmittance characteristic as shown in FIG. 11. Reference numeral 32 denotes a projection lens, reference numeral 33 designates an alignment chart, and reference numeral 34 denotes an LED. The alignment of the apparatus relative to the eye to be examined is effected so that the alignment chart 33 and the front eye part of the eye to be examined become coincident with each other on the television image pickup tube 24.

Although not shown, an illuminating lamp is provided to illuminate the front eye part of the eye to be examined.

Now, where a slide of landscape or the like is used as the fixation chart 30 for measurement of eye refractive power, it is not suitable to use this as the fixation chart for measurement of the shape of the cornea and therefore, a discrete fixation chart for measurement of the shape of cornea is provided at the orthoptic position of the fundus Ef of the eye E to be examined. For example, as shown in FIG. 12, one end of a fiber 38 is disposed at the center of the prism 8 and a light-emitting diode 39 emitting visible light is disposed near the other end of the fiber During the measurement of the shape of the cornea, the illuminating light source 31 is turned off and the light-emitting diode 39 is turned on, and the light-emitting diode 39 emits light to the center of the prism 8 through the fiber 38, whereby the eye E to be examined can watch a clear-cut coalescence point and thus, the eye E to be examined is fixed.

FIG. 13 shows a different embodiment in which the fiber 38 is installed at a different position. One end of the fiber 38 is installed at the central position of the fixation chart 30 for measurement of eye refractive power which is adjacent to the illuminating light source 31, and a light-emitting diode 39 is disposed at the other end of the fiber. In the case of the present embodiment, the fiber 38 also is movable in the direction of the optic axis with the fixation chart 30 and therefore, during the measurement of the shape of the cornea, the eye E to be examined can be caused to watch a more clear-cut coalescence point.

Where a radial pattern is used as the fixation chart 30 for measurement of eye refractive power, this may be used in common for measurement of the shape of cornea, but since the fixation chart 30 is usually installed at the orthoptic position, only an eye in emmetropia to be examined can watch it. Therefore, in order to install the fixation chart 30 at a position corresponding to the refractive power of the eye E to be examined, it is preferable to simply effect measurement of the refractive power before measurement of the shape of cornea. That is, if the light-emitting diode 10 is first caused to emit light and the reflected image from the eye fundus Ef is detected by the detecting element 20 and the fixation chart 30 is moved to a position corresponding to the refractive power thereof, the fixation chart 30 can be clearly seen by the examinee and the gazing axis of the eye E to be examined can be positively fixed. The value of the degree of sphericity necessary for the determination of the position of the fixation chart 30 may be a rough figure and therefore, only a meridian may be processed to shorten the time required for measurement and processing.

Where only the measurement of the shape of cornea is to be effected, the measurement of the refractive power is simply effected in advance in this manner, but where the measurement of the refractive power and the measurement of the shape of the cornea are to be effected continuously, the result of the measurement of the refractive power can be utilized intact. That is, the measurement of the shape of the cornea may be effected after the fixation chart 30 is moved to a position corresponding to the degree of sphericity obtained by the measurement of the refractive power.

FIG. 14 shows the control circuit of the present apparatus. A cornea shape measuring circuit 40 for receiving the signal of the detecting element 9 as an input, an eye refractive power measuring circuit 41 for receiving the signal of the detecting element 21 as an input, a fixation chart control circuit 42 for receiving the signal of the eye refractive power measuring circuit 41 as an input and the controlling the fixation chart 30 and the light source 31 made integral with each other, and a fixation chart illumination control circuit 43 for controlling the light source 31 and the light-emitting diode 39 are connected to a measurement selection control circuit 44 for effecting the selection of measurements, the procedure during continuous measurement and the control of the fixation chart 30 and the illuminating device.

The fixation chart illumination control circuit 43 is a circuit for suitably changing over the turn-on of the light source 31 and the light-emitting diode 39 by the instruction from the measurement selection control circuit 44 and therefore, this control circuit 43 may be omitted where the fixation chart 30 is a radial pattern or the like whose center can be watched.

In an apparatus wherein a fiber 38 is provided because a slide of landscape or the like is used as the fixation chart 30, when measurement of eye refractive power or continuous measurement is selected by the measurement selection control circuit 44, the light source 31 is turned on by the fixation chart illumination control circuit 43 and the signal of the detecting element 21 is input to the eye refractive power measuring circuit 41 while the fixation chart 30 and the light source 31 are moved by the fixation chart control circuit 42, whereby there can be obtained an accurate result of measurement of refractive power from which mechanical short-sightedness has been eliminated.

In the case of continuous measurement, the light source 31 is turned off and the light-emitting diode 39 is turned on by the fixation chart illumination control circuit 43 to create the coalescence point of the fiber 38 which is easy for the eye E to be examined to watch and the eye E to be examined is fixed to thereby effect measurement, and the signal from the detecting element 9 is input to the cornea shape measuring circuit 40, whereby a result of the measurement of the shape of the cornea can be obtained. When the measurement of the shape of the cornea is selected by the measurement selection control circuit 44, the light-emitting diode 39 is turned on by the fixation chart illumination control circuit 43, whereafter the measured value of the shape of the cornea is obtained through a procedure similar to what has been previously described.

When measurement of eye refractive power or continuous measurement is selected by the measurement selection control circuit 44 in a case where a radial pattern is used as the fixation chart 30, measurement of eye refractive power is effected in the same manner as previously described, and when continuous measurement is selected, the fixation chart 30 is moved by the fixation chart control circuit 43 to a position obtained by the measurement of eye refractive power, and the eye E to be examined is caused to watch the fixation chart 30, whereby measurement of the shape of the cornea is effected.

When only the measurement of the shape of cornea is selected by the measurement selection control circuit 44, the data only in the direction of a meridian is input from the detecting element 21 to the eye refractive power measuring circuit 41 in accordance with the procedure during the measurement of eye refractive power and as a result, the fixation chart 30 is moved by the fixation chart control circuit 42, and the eye E to be examined is caused to watch it, whereby ordinary measurement of the shape of the cornea is effected.

Thus, according to the present invention, the eye fundus reflection light does not mix with the cornea shape measuring means and the corneal reflection light does not mix with the refractive power measuring means and therefore, even if measurement is effected with both light sources turned on at the same time, signals having a sufficient S/N ratio can be detected by the respective measuring means.

We claim:

1. An ophthalmic measuring apparatus capable of both measuring the cornea shape and eye refractive power of an eye to be examined, comprising:
   (a) a cornea shape measuring system, having:
      (a1) a projecting optical system for projecting a target image onto the cornea of the eye to be examined,
      (a2) an imaging optical system for reproducing an image of the target reflected at the cornea, and
      (a3) light detecting means for detecting the reflected target image to measure the shape of the cornea,
   (b) a refractive power measuring system, having:
      (b1) a projection optical system for projecting a target image onto the fundus of the eye to be examined,
      (b2) an imaging optical system for reproducing a target image reflected by the fundus of the eye, wherein at least a part of the optical path of each of said imaging optical systems is shared by the other of said imaging optical systems, and
      (b3) light detecting means for detecting the reflected target image to measure the eye refractive power, and
   (c) a fixation chart projecting system, having:
      (c1) first fixation chart means for fixing the gazing axis of the eye during the measurement of the shape of the cornea of the eye,
      (c2) second fixation chart means for fixing the gazing axis of the eye during the measurement of the refractive power of the eye, and
      (c3) driving means for shifting a part of said fixation chart projecting system so that said first fixation chart means is projected from a position corresponding to the refractive power of the eye measured by said refractive power measuring system.

2. An opthalmic measuring apparatus according to claim 1, wherein said first fixation chart means for measuring the shape of the cornea is incorporated in said second fixation chart means for measuring the eye refractive power as a single fixation chart means and wherein said single fixation chart means is commonly used for the cornea shape measurement and the refractive power measurement.

* * * * *

UNITED STATES PATENT AND TRADEMARK OFFICE
CERTIFICATE OF CORRECTION

PATENT NO. : 4,929,076

DATED : May 29, 1990

INVENTOR(S) : Kyoji Sekiguchi

It is certified that error appears in the above-identified patent and that said Letters Patent is hereby corrected as shown below:

On the title page item [75] delete Takashi Masuda.

Signed and Sealed this

Twelfth Day of February, 1991

*Attest:*

HARRY F. MANBECK, JR.

*Attesting Officer*　　　*Commissioner of Patents and Trademarks*

UNITED STATES PATENT AND TRADEMARK OFFICE
CERTIFICATE OF CORRECTION

PATENT NO. : 4,929,076          Page 1 of 3
DATED     : May 29, 1990
INVENTOR(S) : Kyoji Sekiguchi It is certified that error appears in the above-identified patent and that said Letters Patent is hereby corrected as shown below:

ON THE TITLE PAGE

[19] At United States Patent:

"Masuda, et al." should read --Sekiguchi--.

[75] At Inventors:

"Takashi Masuda, Kawasaki; Kyoji Sekiguchi, Yokohama, both of Japan" should read --Koyoji Sekiguchi, Yokahama, Japan--.

[56] References Cited:

U.S. Patent Documents

"4,431,218 2/1984 Nohda" should read --4,431,278 2/1984 Nohda--.

Foreign Patent Documents

"58-29446 7/1959 Japan" should read --58-29446 2/1983 Japan--.

COLUMN 1:

Line 14, "a time." should read --the same time.--.
Line 45, "of" should be deleted.

COLUMN 2:

Line 24, "a time." should read --the same time.--.

UNITED STATES PATENT AND TRADEMARK OFFICE
CERTIFICATE OF CORRECTION

PATENT NO. : 4,929,076

DATED : May 29, 1990

INVENTOR(S) : Kyoji Sekiguchi

It is certified that error appears in the above-identified patent and that said Letters Patent is hereby corrected as shown below:

COLUMN 3:

Line 7, "may illuminated" should read --illuminates--.
    Line 28, "refelction" should read --reflection--.

COLUMN 4:

Line 31, "six openings 17a 17f" should read --six openings 17a-17f--.
    Line 34, "wisely" should read --wise--.

COLUMN 5:

Line 13, "designates" should read --designate--.
    Line 14, "members In" should read --members.  In--.

COLUMN 6:

Line 1, "of cornea" should read --of the cornea--.
    Line 6, "fiber During" should read --fiber.  During--.
    Line 65, "the controlling" should read --controlling--.

UNITED STATES PATENT AND TRADEMARK OFFICE
CERTIFICATE OF CORRECTION

PATENT NO. : 4,929,076

DATED : May 29, 1990

INVENTOR(S) : Kyoji Sekiguchi

It is certified that error appears in the above-identified patent and that said Letters Patent is hereby corrected as shown below:

COLUMN 8:

Line 13, "We claim" should read --What is claimed is--.
    Line 50, "opthalmic" should read --ophthalmic--.

Signed and Sealed this

Twenty-eighth Day of July, 1992

Attest:

DOUGLAS B. COMER

*Attesting Officer*      *Acting Commissioner of Patents and Trademarks*

UNITED STATES PATENT AND TRADEMARK OFFICE
CERTIFICATE OF CORRECTION

PATENT NO. : 4,929,076
DATED : May 29, 1990
INVENTOR(S) : KYOJI SEKIGUCHI, ET AL.

It is certified that error appears in the above-indentified patent and that said Letters Patent is hereby corrected as shown below: On title page, item
[75]    Inventors:

"Koyoji Sekiguchi, Yokohama, Japan" should read
--Kyoji Sekiguchi, Yokohama, Japan--.

Signed and Sealed this

Fourteenth Day of June, 1994

Attest:

BRUCE LEHMAN

*Attesting Officer*    *Commissioner of Patents and Trademarks*